United States Patent
Bodelin

(10) Patent No.: US 6,534,047 B1
(45) Date of Patent: Mar. 18, 2003

(54) MASCARA CONTAINING FILM-FORMING POLYMERS

(75) Inventor: Sophie Bodelin, Vanves (FR)

(73) Assignee: L'Oreal S.A.

(*) Notice: Subject to any disclaimer, the term of this patent is extended or adjusted under 35 U.S.C. 154(b) by 0 days.

(21) Appl. No.: 09/605,435

(22) Filed: Jun. 29, 2000

(30) Foreign Application Priority Data

Jun. 30, 1999 (FR) ............................................. 99 08412

(51) Int. Cl.⁷ ............................. A61K 6/00; A61K 7/00
(52) U.S. Cl. ..................................... 424/70.7; 424/401
(58) Field of Search ................................ 424/70.7, 401

(56) References Cited

U.S. PATENT DOCUMENTS

| | | | |
|---|---|---|---|
| 2,047,398 A | 7/1936 | Voss et al. | 260/2 |
| 2,261,002 A | 10/1941 | Ritter | 260/570 |
| 2,271,378 A | 1/1942 | Scarle | 167/22 |
| 2,273,780 A | 2/1942 | Dittmar | 260/28 |
| 2,375,853 A | 5/1945 | Kirby et al. | 260/583 |
| 2,388,614 A | 11/1945 | Kirby et al. | 167/22 |
| 2,454,547 A | 11/1948 | Bock et al. | 260/567.6 |
| 2,723,248 A | 11/1955 | Wright | 260/45.5 |
| 2,961,347 A | 11/1960 | Floyd | 117/141 |
| 3,206,462 A | 9/1965 | McCarty | 260/256.4 |
| 3,227,615 A | 1/1966 | Korden | 167/87.1 |
| 3,632,559 A | 1/1972 | Basel et al. | 260/78 |
| 3,716,663 A | 2/1973 | Viout et al. | 424/47 |
| 3,874,870 A | 4/1975 | Green et al. | 71/67 |
| 3,912,808 A | 10/1975 | Sokol | 424/71 |
| 3,917,817 A | 11/1975 | Vanlerberghe et al. | 424/70 |
| 3,929,990 A | 12/1975 | Green et al. | 424/78 |
| 3,946,749 A | 3/1976 | Papantoniou | 132/7 |
| 3,966,403 A | 6/1976 | Papantoniou et al. | 8/127.51 |
| 3,966,404 A | 6/1976 | Papantoniou et al. | 8/127.51 |
| 3,966,904 A | 6/1976 | Green et al. | 424/78 |
| 4,001,432 A | 1/1977 | Green et al. | 424/329 |
| 4,005,193 A | 1/1977 | Green et al. | 424/168 |
| 4,013,787 A | 3/1977 | Varlerberghe et al. | 424/70 |
| 4,025,617 A | 5/1977 | Green et al. | 424/78 |
| 4,025,627 A | 5/1977 | Green et al. | 424/248.4 |
| 4,025,653 A | 5/1977 | Green et al. | 424/325 |
| 4,026,945 A | 5/1977 | Green et al. | 260/567.6 |
| 4,027,020 A | 5/1977 | Green et al. | 424/248.56 |
| 4,031,307 A | 6/1977 | DeMartino et al. | 536/114 |
| 4,128,631 A | 12/1978 | Lundmark et al. | 424/70 |
| 4,131,576 A | 12/1978 | Iovine et al. | 260/17.4 |
| 4,137,208 A | 1/1979 | Elliott | 260/29.6 RB |
| 4,165,367 A | 8/1979 | Chakrabarti | 424/47 |
| 4,172,887 A | 10/1979 | Vanlerberghe et al. | 424/70 |
| 4,197,865 A | 4/1980 | Jacquet et al. | 132/7 |
| 4,217,914 A | 8/1980 | Jacquet et al. | 132/7 |
| 4,277,581 A | 7/1981 | Vanlerberghe et al. | 525/420 |
| 4,282,203 A | 8/1981 | Jacquet et al. | 424/47 |
| 4,289,752 A | 9/1981 | Mahieu et al. | 424/47 |
| 4,311,695 A | 1/1982 | Starch | 424/184 |
| 4,349,532 A | 9/1982 | Vanlerberghe et al. | 424/47 |
| 4,366,827 A | 1/1983 | Madrange et al. | 132/7 |
| 4,591,610 A | 5/1986 | Grollier | 524/55 |
| 4,638,822 A | 1/1987 | Grollier et al. | 132/7 |
| 4,660,580 A | 4/1987 | Hoch et al. | 132/7 |
| 4,693,935 A | 9/1987 | Mazurek | 428/352 |
| 4,728,571 A | 3/1988 | Clemens et al. | 428/352 |
| 4,761,273 A | 8/1988 | Grollier et al. | 424/47 |
| 4,839,166 A | 6/1989 | Grollier et al. | 424/71 |
| 4,871,536 A | * 10/1989 | Arraudeau et al. | 424/59 |
| 4,972,037 A | 11/1990 | Garbe et al. | 526/245 |
| 4,996,059 A | 2/1991 | Grollier et al. | 424/71 |
| 5,009,880 A | 4/1991 | Grollier et al. | 424/47 |
| 5,089,252 A | 2/1992 | Grollier et al. | 424/47 |
| 5,534,247 A | * 7/1996 | Franjac et al. | 424/70.7 |
| 5,609,168 A | 3/1997 | Kischka et al. | 132/204 |
| 6,011,126 A | * 1/2000 | Dubief et al. | 525/477 |

FOREIGN PATENT DOCUMENTS

| | | |
|---|---|---|
| DE | 23 30 956 | 1/1974 |
| DE | 44 04 493 | 1/1995 |
| DE | 197 50 520 | 5/1999 |
| EP | 0 095 238 | 11/1983 |
| EP | 0 331 833 | 9/1989 |
| EP | 0 337 354 | 10/1989 |
| EP | 0 412 704 | 2/1991 |

(List continued on next page.)

OTHER PUBLICATIONS

Chemical Abstracts, vol. 131, No. 22, Nov. 29, 1999 (JP 11 292744).
Kirk–Othmer, "Encyclopedia of Chemical Technology", Third Edition, vol. 22, 1983, pp. 332–432.
English language Derwent Abstract of DE 197 50 520.
English language Derwent Abstract of EP 0 847 752.
English language Derwent Abstract of FR 1 564 110.
English language Derwent Abstract of FR 2 077 143.
English language Derwent Abstract of FR 2 080 759.
English language Derwent Abstract of FR 2 320 330.
English language Derwent Abstract of FR 2 336 434.
English language Derwent Abstract of FR 2 357 241.
English language Derwent Abstract of DE 44 04 493.
English language Derwent Abstract of JP 5–178728.
English language Derwent Abstract of JP 5–178729.
English language Derwent Abstract of LU 75370.

Primary Examiner—Thurman K. Page
Assistant Examiner—S. Howard
(74) Attorney, Agent, or Firm—Finnegan, Henderson, Farabow, Garrett & Dunner, L.L.P.

(57) ABSTRACT

The invention relates to a cosmetic composition for coating keratin fibers, comprising a cationic polymer, an anionic polymer and an aqueous dispersion of $C_1$–$C_6$ alkyl (meth)acrylate.

The invention also relates to a process for coating keratin fibers which consists in applying the composition to the keratin fibers.

The composition leads rapidly to a uniform make-up result which has good properties of coating, lengthening and curling the eyelashes, as well as good staying power.

65 Claims, No Drawings

FOREIGN PATENT DOCUMENTS

| | | |
|---|---|---|
| EP | 0 412 707 | 2/1991 |
| EP | 0 492 657 | 7/1992 |
| EP | 0 582 152 | 2/1994 |
| EP | 0 685 219 | 12/1995 |
| EP | 0 847 752 | 6/1998 |
| FR | 1 222 944 | 6/1960 |
| FR | 1 492 597 | 8/1967 |
| FR | 1 564 110 | 4/1969 |
| FR | 1 580 545 | 9/1969 |
| FR | 1 583 363 | 10/1969 |
| FR | 2 077 143 | 10/1971 |
| FR | 2 080 759 | 11/1971 |
| FR | 2 162 025 | 7/1973 |
| FR | 2 190 406 | 2/1974 |
| FR | 2 252 840 | 6/1975 |
| FR | 2 265 781 | 10/1975 |
| FR | 2 265 782 | 10/1975 |
| FR | 2 270 846 | 12/1975 |
| FR | 2 280 361 | 2/1976 |
| FR | 2 316 271 | 1/1977 |
| FR | 2 320 330 | 3/1977 |
| FR | 2 336 434 | 7/1977 |
| FR | 2 350 384 | 12/1977 |
| FR | 2 357 241 | 2/1978 |
| FR | 2 368 508 | 5/1978 |
| FR | 2 383 660 | 10/1978 |
| FR | 2 393 573 | 1/1979 |
| FR | 2 413 907 | 8/1979 |
| FR | 2 439 798 | 5/1980 |
| FR | 2 470 596 | 6/1981 |
| FR | 2 472 382 | 7/1981 |
| FR | 2 505 348 | 11/1982 |
| FR | 2 519 863 | 7/1983 |
| FR | 2 528 699 | 12/1983 |
| FR | 2 530 465 | 1/1984 |
| FR | 2 542 997 | 9/1984 |
| FR | 2 598 611 | 11/1987 |
| FR | 2 739 288 | 4/1997 |
| GB | 0 839 805 | 6/1960 |
| GB | 1 110 240 | 4/1968 |
| JP | 5-178728 | 7/1993 |
| JP | 5-178729 | 7/1993 |
| LU | 75370 | 7/1976 |
| LU | 75371 | 7/1976 |
| WO | WO 93/23009 | 11/1993 |
| WO | WO 93/23446 | 11/1993 |
| WO | WO 95/00578 | 1/1995 |
| WO | WO 95/15741 | 6/1995 |
| WO | WO 95/34271 | 12/1995 |
| WO | WO 98/19653 | 5/1998 |

\* cited by examiner

MASCARA CONTAINING FILM-FORMING POLYMERS

The present invention relates to a composition for coating keratin fibers comprising a mixture of film-forming polymers. The invention also relates to the use of this composition for making up keratin fibers, as well as to a process for making up these fibers. The composition and the make-up process according to the invention are suitable for substantially longilinear human keratin fibers such as the eyelashes, the eyebrows and the hair, including false eyelashes and hairpieces. The composition can be a make-up composition, a make-up base, a composition to be applied to a make-up, also known as a top-coat, or, alternatively, a composition for cosmetically treating keratin fibers. According to one embodiment, the invention relates to a mascara.

Compositions for coating the eyelashes, known as mascaras, generally comprise at least one wax and at least one film-forming polymer. A mascara is typically used to deposit a make-up film on the eyelashes and coat them. Published PCT Application No. WO-A-95/15741, for example, describes such compositions. Users expect these products to have good a cosmetic properties, such as adhesion to the eyelashes, lengthening or a curling of the eyelashes, or, alternatively, good staying power of the mascara over time, in particular good resistance to rubbing, for example with the fingers or fabrics (handkerchiefs, towels).

To give the eyelashes a lengthening effect, French Patent Application No. FR-A-2 528 699 proposes a mascara comprising waxes and a combination of anionic polymer and cationic polymer. However, these compositions may not allow optimum curling of the eyelashes.

One aspect of the present invention is to provide a composition for making up keratin fibers, including fibers such as the eyelashes, which may apply easily and may provide for good curling of the keratin fibers.

The inventor has discovered that such a composition may be obtained using a specific combination of film-forming polymers.

More specifically, one aspect of the invention is a composition for making up keratin fibers comprising at least one film-forming polymer comprising at least one cationic film-forming polymer and at least one anionic film-forming polymer, characterized in that it comprises an aqueous dispersion of at least one $C_1$–$C_6$ alkyl (meth)acrylate nonionic film-forming polymer.

The composition according to the invention may apply easily and may attach well to keratin fibers such as the eyelashes. It has been found that the make-up results such as the coating, lengthening, and curling of the eyelashes may be obtained quickly and easily after applying the composition to the eyelashes. The make-up may be comfortable for the user to wear, and it may be easily removed with conventional make-up-removing agents.

One embodiment of the invention is a process for coating keratin fibers, such as the eyelashes, comprising applying a composition as defined above to the keratin fibers.

Another embodiment of the invention is the use of a composition as defined above to curl and/or lengthen and/or coat the eyelashes, and/or to obtain a fast make-up, and/or a make-up which is easy to apply, and/or which has good staying power.

The expression "film-forming polymer" means a polymer which by itself, or in the presence of a plasticizer, leads to an isolable film.

The composition according to the invention comprises an aqueous dispersion of at least one nonionic film-forming $C_1$–$C_6$ alkyl (meth)acrylate polymer, such as a polymer derived from at least one $C_1$–$C_6$ alkyl (meth)acrylate monomer. These polymers can be chosen from $C_1$–$C_4$ alkyl (meth)acrylate polymers, such as copolymers derived from at least one monomer chosen from $C_1$–$C_4$ alkyl acrylate and $C_1$–$C_4$ alkyl methacrylate. $C_1$–$C_4$ alkyl (meth)acrylates which may be mentioned include, for example, methyl (meth)acrylate, ethyl (meth)acrylate, propyl (meth)acrylate, and butyl (meth)acrylate. A copolymer derived from ethyl acrylate and methyl methacrylate, such as the one sold under the name DAITOSOL 5000 AD by Daito Kasey Kogyo, may be used.

The aqueous dispersion of nonionic film-forming alkyl (meth)acrylate polymer can comprise polymer particles ranging from 10 nm to 500 nm in size. In another embodiment, the particles can range from 20 nm to 300 nm in size.

The expression "aqueous dispersion of polymer", which is generally known as a latex or pseudo-latex, means a phase containing water and optionally a water-soluble compound, in which the polymer is dispersed directly in the form of particles.

In practice, the nonionic film-forming $C_1$–$C_6$ alkyl (meth)acrylate polymer can be present in the composition according to the invention in a solids content ranging from 0.1% to 15% by weight, relative to the total weight of the composition. In another embodiment, the solid content can range from 0.5% to 8% by weight.

According to one embodiment, the composition according to the invention may contain any known anionic polymer, including a non-crosslinked anionic polymer, or any known cationic polymer.

These polymers can be used in dissolved form or in the form of aqueous dispersions of solid polymer particles.

The anionic polymers generally used can be polymers comprising groups derived from at least one monomer chosen from carboxylic, sulfonic, and phosphoric acid, and can have a weight-average molecular weight ranging from about 500 to about 5,000,000.

1) The carboxylic groups can be borne by unsaturated mono- or dicarboxylic acid monomers such as those corresponding to formula (I):

wherein n is an integer from 0 to 10,

A can be a methylene group, optionally connected to the carbon atom of the unsaturated group or to the neighboring methylene group when n is greater than 1 via a hetero atom such as oxygen or sulphur;

$R_5$ is chosen from a hydrogen atom, a phenyl group, and a benzyl group;

$R_3$ is chosen from a hydrogen atom, lower alkyl groups, and carboxyl groups; and $R_4$ is chosen from a hydrogen atom, lower alkyl groups, $CH_2$—COOH, phenyl groups, and benzyl groups.

In the abovementioned formula and throughout the disclosure, the expressions "lower alkyl" and "lower alkyl radical" can denote a group containing 1 to 8 carbon atoms such as, for example, methyl and ethyl.

The anionic polymers containing carboxylic groups which are useful according to the invention include:

A) Homo- and copolymers derived from at least one monomer chosen from acrylic and methacrylic acid and the salts of the homo- and copolymers (such as alkali metal, alkaline earth metal, and ammonium salts), including the products sold under the names VERSICOL E or VERSICOL K by Allied Colloid, ULTRAHOLD by BASF, and DARVAN 7 by Vanderbilt. The copolymers derived from acrylic acid and acrylamide sold in the form of their sodium salt under the names RETEN 421, RETEN 423, or RETEN 425 by Hercules, and the sodium salts of polyhydroxycarboxylic acids.

B) Copolymers derived from (i) at least one monomer chosen from acrylic and methacrylic acids and (ii) a monoethylenic monomer such as ethylene, styrene, vinyl esters, and acrylic or methacrylic acid esters. These copolymers can be grafted onto a polyalkylene glycol such as polyethylene glycol. Such polymers are described in, for example, French Patent No. 1,222,944, and German Patent Application No. 2,330,956, the disclosures of which are incorporated by reference herein. Mention may be made of copolymers whose chain comprises an optionally N-alkylated and/or hydroxyalkylated acrylamide unit, such as those described in Luxembourg Patent Application Nos. 75370 and 75371, the disclosures of which are incorporated by reference herein, or sold under the name QUADRAMER by American Cyanamid. Mention may also be made of copolymers derived from acrylic acid and $C_1$–$C_4$ alkyl methacrylate and terpolymers derived from vinylpyrrolidone, (meth)acrylic acid and (meth) acrylate of a $C_1$–$C_{20}$ alkyl, for example of lauryl (such as the product sold by ISP under the name ACRYLIDONE LM), of tert-butyl (LUVIFLEX VMB 70 sold by BASF) or of methyl (STEPANHOLD EXTRA sold by Stepan) and methacrylic acid/ethyl acrylate/tert-butyl acrylate terpolymers, such as the product sold under the name LUVIMER100 P by BASF.

C) Copolymers derived from crotonic acid, such as those whose chain comprises units derived from at least one monomer chosen from vinyl acetate and propionate, and optionally other monomers chosen from allylic and methallylic esters, vinyl ether and vinyl ester of saturated, linear, and branched carboxylic acids containing a long hydrocarbon-based chain such as those comprising at least 5 carbon atoms, it being possible for these polymers to be optionally grafted, or, alternatively, a vinyl, allylic, or methallylic ester of an α- or β-cyclic carboxylic acid. Such polymers are described, inter alia, in French Patent Nos. 1,222,944; 1,580,545; 2,265,782; 2,265,781; 1,564,110; and 2,439,798, the disclosures of which are incorporated by reference herein. Commercial products falling within this category include the resins 28-29-30, 26-13-14, and 28-13-10 sold by National Starch.

D) Copolymers derived from at least one monomer chosen from monounsaturated $C_4$–$C_8$ carboxylic acids and anhydrides of such acids such as:
copolymers derived from (i) at least one monomer chosen from maleic, fumaric, and itaconic acids and anhydrides of each of said acids, and (ii) at least one monomer chosen from vinyl esters, vinyl ethers, vinyl halides, phenyl vinyl derivatives, acrylic acid and esters, the anhydride functions of these copolymers optionally being monoesterified or monoamidated. Such polymers are described in, for example, U.S. Pat. Nos. 2,047,398; 2,723,248; and 2,102,113, as well as Great Britain Patent No. 839,805, the disclosures of which are incorporated by reference herein. Such polymers include those sold under the names GANTREZ AN, GANTREZ ES, and AVANTAGE CP sold by ISP.

copolymers comprising (i) at least one unit derived from maleic, citraconic, and itaconic anhydride monomers and (ii) at least one unit derived from allylic and methallylic ester monomers optionally comprising at least one unit derived from acrylamide, methacrylamide, α-olefin, acrylic, and methacrylic esters, acrylic and methacrylic acids, and vinylpyrrolidone groups in their chain, the anhydride functions of these copolymers optionally being monoesterified or monoamidated.

These polymers are described in, for example, French Patent Nos. 2,350,384 and 2,357,241, the disclosures of which are incorporated by reference herein.

E) Polyacrylamides comprising carboxylate groups, and mixtures thereof.

2) The polymers comprising sulphonic groups can be polymers comprising vinylsulphonic, styrenesulphonic, naphthalenesulphonic, or acrylamidoalkylsulphonic units or, alternatively, sulphonic polyesters.

These polymers can be chosen from:

polyvinylsulphonic acid salts with a weight-average molecular weight ranging from 1000 to 100,000, as well as copolymers with an unsaturated comonomer such as acrylic or methacrylic acids and esters thereof, as well as acrylamide or derivatives thereof, vinyl ethers, and vinylpyrrolidone;

polystyrenesulphonic acid salts, the sodium salts having a weight-average molecular weight of about 500,000 and of about 100,000, sold, respectively, under the names FLEXAN 500 and FLEXAN 130 by National Starch. These compounds are described in French Patent No. FR 2,198,719, the disclosure of which is incorporated by reference herein;

polyacrylamide sulphonic acid salts such as those mentioned in U.S. Pat. No. 4,128,631, the disclosure of which is incorporated by reference herein including, for example, polyacrylamidoethylpropanesulphonic acid sold under the name COSMEDIA POLYMER HSP 1180 by Henkel;

sulphonic polyesters bearing at least one group —$SO_3M$, wherein M is chosen from a hydrogen atom, an ammonium ion $NH_4^+$, and a metal ion. The copolyester can be, for example, a copolymer derived from (i) at least one dicarboxylic acid, (ii) at least one diol, and (iii) at least one difunctional aromatic monomer bearing a group —$SO_3M$ wherein M is chosen from a hydrogen atom, an ammonium ion, and a metal ion.

The dicarboxylic acid can be chosen from phthalic acid, isophthalic acid, and terephthalic acid. The diol can be chosen from ethylene glycol, diethylene glycol, triethylene glycol, 1,3-propanediol, 1,4-cyclohexanedimethanol, and 1,4-butanediol. The difunctional aromatic monomer bearing the group —$SO_3M$ can be chosen from sulphoisophthalic acid, such as the sodium salt of 5-sulphoisophthalic acid, sulphoterephthalic acid, sulphophthalic acid, and 4-sulphonaphthalene-2,7-dicarboxylic acid.

A suitable polyester which can be used is a polyester having repeating units derived from (i) isophthalic acid, (ii) diol and (iii) sulphoisophthalic acid, including, for example, the sulphopolyesters obtained by condensation of diethylene glycol, of cyclohexanedimethanol, of isophthalic acid, and of sulphoisophthalic acid. Sulphonic polyesters which can be used are those sold under the names AQ55S, AQ38S, and AQ29S by Eastman.

An anionic polymer which can also be used is (deoxy) ribonucleic acid.

According to the invention, the anionic polymers may be chosen from acrylic acid copolymers such as the acrylic acid/ethyl acrylate/N-tert-butylacrylamide terpolymers sold under the name ULTRAHOLD STRONG by BASF, copolymers derived from crotonic acid, such as the vinyl acetate/vinyl tert-butylbenzoate/crotonic acid terpolymers and the crotonic acid/vinyl acetate/vinyl neododecanoate terpolymers sold under the name RESIN 28-29-30 by National Starch, polymers derived from (i) at least one monomer chosen from maleic, fumaric, and itaconic acids and the anhydrides of each such acid and (ii) at least one monomer chosen from vinyl esters, vinyl ethers, vinyl halides, phenylvinyl derivatives, acrylic acid and esters of acrylic acid, such as the methyl vinyl ether/monoesterified maleic anhydride copolymers sold, for example, under the name GANTREZ by ISP, the copolymers derived from methacrylic acid and methyl methacrylate sold under the name EUDRAGIT L by Rohm Pharma, the methacrylic acid/methyl methacrylate/$C_1$–$C_4$ alkyl acrylate/acrylic acid or $C_1$–$C_4$ hydroxyalkyl methacrylate copolymers sold in the form of dispersions under the name AMERHOLD DR 25 by Amerchol or under the name ACUDYNE 255 by Rohm & Haas, the copolymers derived from methacrylic acid and ethyl acrylate sold under the name LUVIMER MAEX or LUVIMER MAE by BASF, and the vinyl acetate/crotonic acid copolymers and vinyl acetate/crotonic acid copolymers grafted with polyethylene glycol sold under the name ARISTOFLEX A by BASF, the acrylic or methacrylic acid homopolymers sold, for example, under the name VERSICOLE 5 or poly(sodium methacrylate) sold under the name DARVAN 7 by Vanderbilt, and mixtures thereof.

The anionic polymers which may be used include those chosen from non-crosslinked anionic polymers such as the methyl vinyl ether/monoesterified maleic anhydride copolymers sold under the name GANTREZ ES 425 by ISP, the acrylic acid/ethyl acrylate/N-tert-butylacrylamide terpolymers sold under the name ULTRAHOLD STRONG by BASF, the copolymers derived from methacrylic acid and methyl methacrylate sold under the name EUDRAGIT L by Rohm Pharma, the vinyl acetate/vinyl tert-butylbenzoate/crotonic acid terpolymers and the crotonic acid/vinyl acetate/vinyl neododecanoate terpolymers sold under the name RESIN 28-29-30 by National Starch, the copolymers derived from methacrylic acid and ethyl acrylate sold under the name LUVIMER MAEX or LUVIMER MAE by BASF, the vinylpyrrolidone/acrylic acid/lauryl methacrylate terpolymers sold under the name ACRYLIDONE LM by ISP and the acrylic or methacrylic acid homopolymers sold, for example, under the name VERSICOLE 5 or poly(sodium methacrylate) sold under the name DARVAN 7 by Vanderbilt, and mixtures thereof.

According to an aspect of the invention, it is also possible to use anionic polymers in latex or pseudolatex form, i.e., in the form of a dispersion of insoluble polymer particles.

3) According to the invention, it is also possible to use anionic polymers of grafted silicone type comprising a polysiloxane portion and a non-silicone organic chain portion, one of the two portions constituting the main chain of the polymer, the other being grafted onto the said main chain. These polymers are described, for example, in European Patent Application Nos. EP-A-0 412 704, EP-A-0 412 707, EP-A-0 640 105 and WO 95/00578, EP-A-0 582 152 and WO 93/23009, and U.S. Pat. Nos. 4,693,935, 4,728,571, and 4,972,037, the disclosures of which are incorporated by reference herein.

Such polymers are, for example, the copolymers which can be obtained by radical polymerization from a monomer mixture comprising:

a) 50 to 90% by weight of tert-butyl acrylate;
b) 1 to 40% by weight of acrylic acid;
c) 5 to 40% by weight of silicone macromer of formula (II):

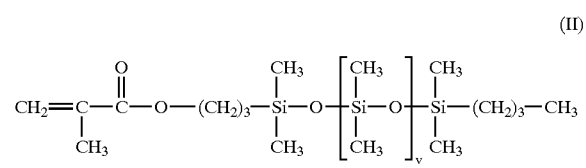

with v being a number ranging from 5 to 700; the weight percentages being calculated relative to the total weight of the monomers.

One family of silicone polymers containing a polysiloxane skeleton grafted with non-silicone organic monomers which is useful for carrying out the present invention includes silicone polymers whose structure comprises the unit of formula (III):

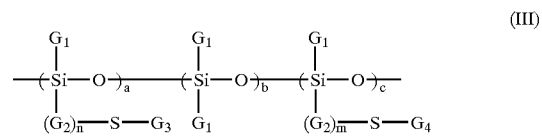

wherein:
the radicals $G_1$, which may be identical or different, are independently chosen from hydrogen, $C_1$–$C_{10}$ alkyl radicals, and a phenyl radical;
the radicals $G_2$, which may be identical or different, are independently chosen from $C_1$–$C_{10}$ alkylene groups;
$G_3$ is chosen from polymeric residues resulting from the (homo)polymerization of at least one anionic monomer containing ethylenic unsaturation, said residues being identical or different if $a \geq 2$;
$G_4$ is chosen from polymeric residues resulting from the (homo)polymerization of at least one hydrophobic monomer containing ethylenic unsaturation, said residues being identical or different if $a \geq 2$;
m and n are equal to 0 or 1;
a is an integer ranging from 0 to 50;
b is an integer ranging from 10 to 350; and
c is an integer ranging from 0 to 50, with the proviso that one of the parameters a and c is other than 0.

In one embodiment, the unit of formula (III) above has at least one, and possibly all, of the following characteristics:
the radicals $G_1$ are chosen from $C_1$–$C_{10}$ alkyl radicals such as, for example, a methyl radical;
n is non-zero; and
the radicals $G_2$ are chosen from divalent $C_1$–$C_3$ radicals such as, for example, a propylene radical;
$G_3$ is chosen from polymeric radicals resulting from the (homo)polymerization of at least one monomer such as a carboxylic acid containing ethylenic unsaturation such as, for example, acrylic acid and/or methacrylic acid;
$G_4$ is chosen from polymeric radicals resulting from the (homo)polymerization of at least one monomer such as a $C_1$–$C_{10}$ alkyl (meth)acrylate such as, for example, isobutyl and methyl (meth)acrylate.

According to one embodiment of the invention, the unit of formula (III) above can also have all of the following characteristics:

the radicals $G_1$ denote an alkyl radical, such as a methyl radical;

n is non-zero; and the radicals $G_2$ are chosen from divalent $C_1$–$C_3$ radicals, such as a propylene radical;

$G_3$ is chosen from polymeric radicals resulting from the (homo)polymerization of at least one monomer such as a carboxylic acid containing ethylenic unsaturation such as, for example, acrylic acid and/or methacrylic acid;

c is equal to zero.

Examples of grafted silicone polymers include polydimethylsiloxanes (PDMSs) onto which are grafted, via a connecting member of thiopropylene type, mixed polymer units derived from the poly(meth)acrylic acid type and the poly (alkyl (meth)acrylate) type, such as poly(isobutyl (meth) acrylate).

The grafted silicone polymers of formula (III) of polymethyl/methylsiloxane structure containing 3-thiopropyl polymethacrylic acid groups and 3-thiopropyl polymethyl methacrylate groups and the grafted silicone polymers of formula (III) of polymethyl/methylsiloxane structure containing 3-thiopropyl polyacrylic acid groups are suitably used.

According to one aspect of the invention, the anionic polymer(s) can be present in an amount ranging from 0.01% to 20% by weight. In another embodiment, the amount may range from 0.05% to 15% by weight. In yet another embodiment, the amount may range from 0.1% to 7% by weight, relative to the total weight of the composition.

The cationic polymers which can be used in accordance with the present invention can be chosen from all those already known, including those described in European Patent Application No. EP-A-0,337,354, and in French Patent Application Nos. FR-A-2,270,846; 2,383,660; 2,598, 611; 2,470,596; and 2,519,863, the disclosures of which are incorporated by reference herein.

Even more generally, for the purposes of the present invention, the expression "cationic polymer" includes any polymer containing cationic groups or groups which can be ionized into cationic groups.

Suitable cationic polymers may be chosen from those which contain units chosen from primary, secondary, tertiary, and quaternary amine groups which can either form part of the main polymer chain or can be borne by a lateral substituent directly connected thereto.

The cationic polymers used generally have a number-average molecular weight ranging from approximately 500 to approximately $5 \times 10^6$. In another embodiment, the number-average molecular weight ranges from approximately $10^3$ to approximately $3 \times 10^6$.

Among the cationic polymers which may be mentioned more particularly are known polymers such as polyamines, polyaminoamides, and polyquaternary ammoniums.

One family of cationic polymers is the family of silicone cationic polymers. Among these polymers which may be mentioned are, for example:

(a) the silicone polymers corresponding to formula (IV):

$$R^6{}_a G^5{}_{3-a}-Si(OSiG^6{}_2)_n-(OSiG^7{}_b R^7{}_{2-b})_m-O-SiG^8{}_{3-a}-R^8{}_a \quad (IV)$$

wherein:

$G^5$, $G^6$, $G^7$ and $G^8$, which may be identical or different, are independently chosen from a hydrogen atom, a phenyl radical, a OH radical, $C_1$–$C_{18}$ alkyl radicals such as, for example, methyl, $C_2$–$C_{18}$ alkenyl radicals, and $C_1$–$C_{18}$ alkoxy radicals;

a and a', which may be identical or different, are independently chosen from 0 to 3; in one embodiment, a and a' are both 0;

b is chosen from 0 and 1; in one embodiment, b is 1; and m and n are numbers such that the sum (n+m) can range from 1 to 2000. In one embodiment, the sum can range from 50 to 150. It is possible for n to denote a number from 0 to 1999. In another embodiment, n can range from 49 to 149. It is possible for m to denote a number ranging from 1 to 2000. In a certain embodiment, m can range from 1 to 10;

$R^6$, $R^7$ and $R^8$, which may be identical or different, are independently chosen from monovalent radicals of formula:

$$-C_q H_{2q} O_s R^9{}_t L$$

wherein q is a number chosen from 1 to 8;

s and t, which may be identical or different, are equal to 0 or 1;

$R^9$ is chosen from unsubstituted and hydroxylated alkylene groups; and

L is an optionally quaternized amino group chosen from:

NR"—$CH_2$—$CH_2$—N'(R")$_2$

N(R")$_2$ $N^{\oplus}(R")_3 A^-$ $N^{\oplus}H(R")_2 A^-$ $N^{\oplus}H_2(R")A^-$

N(R")—$CH_2$—$CH_2$—$N^{\oplus}R"H_2 A^-$ wherein:

R" is independently chosen from hydrogen, phenyl, benzyl, and monovalent saturated hydrocarbon-based radicals, for example an alkyl radical containing from 1 to 20 carbon atoms; and $A^-$ is chosen from a halide ion such as, for example, fluoride, chloride, bromide, and iodide.

Products corresponding to this definition include, for example, the polysiloxanes referred to in the CTFA dictionary as "amodimethicone" and corresponding to formula (V):

$$HO-\left[\begin{array}{c}CH_3\\|\\Si-O\\|\\CH_3\end{array}\right]_{x'}\left[\begin{array}{c}OH\\|\\Si-O\\|\\(CH_2)_3\\|\\NH\\|\\(CH_2)_2\\|\\NH_2\end{array}\right]_{y'}-H \quad (V)$$

in which x' and y' are integers dependent on the molecular weight, generally such that the said molecular weight ranges from approximately 5000 to approximately 20,000.

One product corresponding to formula (IV) is the polymer referred to in the CTFA dictionary as "trimethylsilylamodimethicone", corresponding to formula (VI):

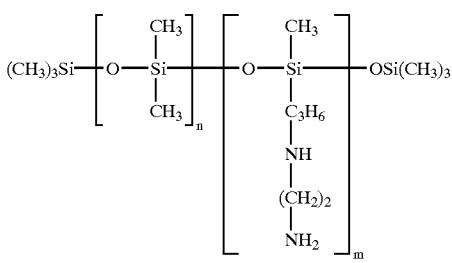

(VI)

wherein n and m have the meanings given above for formula (IV).

A commercial product corresponding to this definition includes a mixture (90/10 by weight) of a polydimethylsiloxane containing aminoethyl aminoisobutyl groups and of a polydimethylsiloxane sold under the name Q2-8220 by Dow Corning.

Such polymers are described, for example, in European Patent Application No. EP-A-95,238, the disclosure of which is incorporated by reference herein.

Other polymers corresponding to formula (IV) are the silicone polymers corresponding to formula (VII):

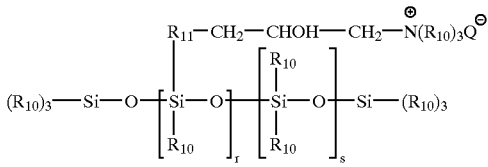

(VII)

wherein:
- $R_{10}$ is identical or different and is independently chosen from monovalent hydrocarbon-based radicals containing from 1 to 18 carbon atoms such as, for example, $C_1$–$C_{18}$ alkyl or $C_2$–$C_{18}$ alkenyl radicals, such as methyl;
- $R_{11}$ is identical or different and is independently chosen from divalent hydrocarbon-based radicals such as, for example, $C_1$–$C_{18}$ alkylene radicals and divalent $C_1$–$C_{18}$ radicals, for example $C_1$–$C_8$, alkylenoxy radicals;
- $Q^-$ is chosen from halide ions, such as chloride;
- r represents an average statistical value ranging from 2 to 20. In one embodiment, the value can range from 2 to 8;
- s represents an average statistical value ranging from 20 to 200. In a certain embodiment, the value ranges from 20 to 50.

Such polymers are described more particularly in U.S. Pat. No. 4,185,087, the disclosure of which is incorporated by reference herein.

(b) the compounds of formula: NH—[(CH$_2$)$_3$—Si[OSi(CH$_3$)$_3$]]$_3$ corresponding to the CTFA name "aminobispropyldimethicone".

One polymer falling within this category is the polymer sold by Union Carbide under the name "UCAR SILISONE ALE 56".

When these silicone polymers are used, one embodiment is their joint use with cationic and/or nonionic surfactants. It is possible, for example, to use the product sold under the name "CATIONIC EMULSION DC 929" by Dow Corning, which comprises, besides amodimethicone, a cationic surfactant, comprising a mixture of products corresponding to formula (VIII):

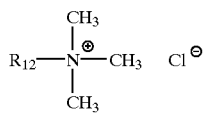

(VIII)

wherein:
- $R_{12}$ is chosen from alkenyl and alkyl radicals containing from 14 to 5 22 carbon atoms, derived from tallow fatty acids,
- in combination with a nonionic surfactant of formula:

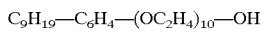

known under the name "NONOXYNOL 10".

Another commercial product which can be used according to the invention is the product sold under the name "DOW CORNING Q2 7224" by Dow Corning comprising, in combination, trimethylsilylamodimethicone of formula (IV), a nonionic surfactant of formula:

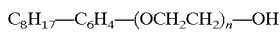

wherein:
n=40, also known as octoxynol-40, and
another nonionic surfactant of formula:

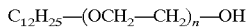

wherein
n=6, also known as isolaureth-6, and glycol.

The polymers of polyamine, polyaminoamide, and polyquaternary ammonium type which can be used in accordance with the present invention and which can be mentioned in particular are those described in French Patents Nos. 2,505,348 and 2,542,997, the disclosures of which are incorporated by reference herein. Among these polymers which may be mentioned are, for example:

(1) Quaternized or non-quaternized vinylpyrrolidone/dialkylaminoalkyl acrylate or methacrylate copolymers, such as the products sold under the name "GAFQUAT" by ISP, such as, for example, GAFQUAT 734, GAFQUATE 755, or GAFQUAT HS100, or, alternatively the product known as "COPOLYMER 937". These polymers are described in detail French Patent Nos. 2,077,143 and 2,393,573, the disclosures of which are incorporated by reference herein.

(2) Cellulose ether derivatives, including hydroxy($C_1$–$C_4$) alkylcelluloses, comprising quaternary ammonium groups described in French Patent No. 1,492,597, and the polymers sold under the names "JR" (JR 400, JR 125, JR 30M) or "LR" (LR 400, LR 30M) by Union Carbide Corporation. These polymers are also defined in the CTFA dictionary as quaternary ammoniums of hydroxyethylcellulose which has reacted with an epoxide (in particular epichlorohydrin) substituted with a trimethylammonium group.

(3) Cationic cellulose derivatives such as cellulose copolymers or cellulose derivatives grafted with a water-soluble quaternary ammonium monomer, and described in particular in U.S. Pat. No. 4,131,576, the disclosure of which is incorporated by reference herein, such as hydroxyalkylcelluloses, for example hydroxymethyl-, hydroxyethyl- or hydroxypropylcelluloses grafted in particular with a methacryloylethyltrimethylammonium, methacrylamidopropyltrimethylammonium, or dimethyldiallylammonium salt.

The commercial products corresponding to this definition are, more particularly, the products sold under the names "CELQUAT L 200" and "CELQUAT H 100" by National Starch.

(4) The cationic polysaccharides described more particularly in U.S. Pat. Nos. 3,589,578 and 4,031,307, the disclosures of which are incorporated by reference herein, and the product sold under the name "JAGUAR C13 S" sold by Meyhall.

(5) Polymers comprising piperazinyl units and divalent alkylene or hydroxyalkylene radicals containing straight or branched chains, optionally interrupted with at least one heteroatom chosen from oxygen, sulphur, and nitrogen, or with aromatic or heterocyclic rings, as well as the oxidation and quaternization products of these polymers. Such polymers are described in particular in French Patent Nos. 2,162,025 and 2,280,361, the disclosures of which are incorporated by reference herein.

(6) Water-soluble polyaminoamides prepared, for example, by polycondensation of an acidic compound with a polyamine; these polyaminoamides can be crosslinked with an epihalohydrin, a diepoxide, a dianhydride, an unsaturated dianhydride, a bis-unsaturated derivative, a bishalohydrin, a bis-azetidinium, a bis-haloacyldiamine, a bisalkyl halide, or with an oligomer resulting from the reaction of a difunctional compound which is reactive with respect to a bis-halohydrin, a bis-azetidinium, a bis-haloacyldiamine, a bis-alkyl halide, an epihalohydrin, a diepoxide or a bisunsaturated derivative, the crosslinking agent being used in proportions ranging from 0.025 to 0.35 mol per amine group of the polyaminoamide; these polyaminoamides can be alkylated or, if they comprise one or more tertiary amine functions, can be quaternized. Such polymers are described in particular in French Patent Nos. 2,252,840 and 2,368,508, the disclosures of which are incorporated by reference herein.

(7) Polyaminoamide derivatives resulting from the condensation of polyalkylene polyamines with polycarboxylic acids, followed by an alkylation with difunctional agents. Mention may be made, for example, of adipic acid/dialkylaminohydroxyalkyldialkylenetriamine polymers in which the alkyl radical comprises from 1 to 4 carbon atoms and suitably denotes methyl, ethyl or propyl. Such polymers are described in particular in French Patent No. 1,583,363, the disclosure of which is incorporated by reference herein.

Among these derivatives which may be mentioned more particularly are the adipic acid/dimethylaminohydroxypropyl/diethylenetriamine polymers sold under the name "CARTARETINE F, CARTARETINE F4, or CARTARETINE F8" by Sandoz.

(8) Polymers obtained by reacting a polyalkylene (divalent aliphatic group) polyamine comprising two primary amine groups and at least one secondary amine group with a dicarboxylic acid chosen from diglycolic acid and saturated aliphatic dicarboxylic acids containing from 3 to 8 carbon atoms. The molar ratio of the polyalkylene polyamine to the dicarboxylic acid is from 0.8:1 to 1.4:1, the polyaminoamide resulting therefrom being made to react with epichlorohydrin in a molar ratio of epichlorohydrin relative to the secondary amine group in the polyaminoamide from 0.5:1 to 1.8:1. Such polymers are described in particular in U.S. Pat. Nos. 3,227,615 and 2,961,347, the disclosures of which are incorporated y reference herein.

Polymers of this type include those sold under the name "HERCOSETTE 57" by Hercules Inc. or, alternatively, under the name "PD 170" or "DELSETTE 101" by Hercules in the case of the adipic acid/epoxypropyl/diethylenetriamine copolymer.

(9) Copolymers derived from at least one methyidiallylamine and diallyidimethylammonium, such as homopolymers or copolymers comprising, as main constituent of the chain, units corresponding to formulae (IX) or (IX'):

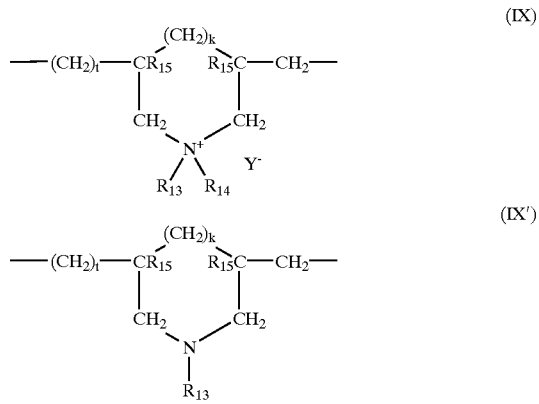

wherein:
k and t are equal to 0 or 1, the sum k+t being equal to 1;
$R_{15}$ is identical or different and is independently chosen from a hydrogen atom and a methyl radical;
$R_{13}$ and $R_{14}$, which are identical or different, are independently chosen from alkyl groups containing from 1 to 22 carbon atoms, hydroxyalkyl groups in which the alkyl group contains 1 to 5 carbon atoms, and lower amidoalkyl groups, i.e. $C_1$–$C_8$; alternatively, $R_{13}$ and $R_{14}$ can denote, together with the nitrogen atom to which they are attached, heterocyclic groups such as piperidyl or morpholinyl;
$Y^-$ is an anion which may be chosen from, for example, bromide, chloride, acetate, borate, citrate, tartrate, bisulphate, bisulphite, sulphate, and phosphate.

These polymers are described in particular in French Patent No. 2,080,759, and in its certificate of addition 2,190,406, the disclosure of which is incorporated by reference herein.

Mention may be made, for example, of the diallyldimethylammonium chloride homopolymer sold under the name "MERQUAT 100" by Merck and the copolymers derived from diallyldimethylammonium chloride and from acrylamide sold under the name "MERQUAT 550".

(10) The diquaternary ammonium polymer containing repeating units corresponding to formula (X):

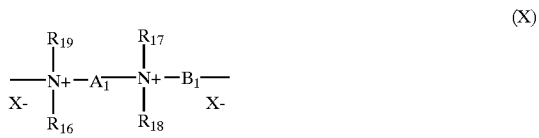

wherein:
$R_{16}$, $R_{17}$, $R_{18}$ and $R_{19}$, which may be identical or different, are independently chosen from aliphatic, alicyclic, and arylaliphatic radicals containing from 1 to 20 carbon atoms, and lower hydroxyalkyl ($C_1$–$C_8$) aliphatic radicals, or
$R_{16}$, $R_{17}$, $R_{18}$ and $R_{19}$, together or separately, constitute, with the nitrogen atoms to which they are attached, heterocycles optionally containing a second hetero atom other than nitrogen or, alternatively, —$R_{16}$, $R_{17}$, $R_{18}$ and $R_{19}$ are chosen from linear and branched $C_1$–$C_6$ alkyl radicals substituted with at least one group chosen from nitrile, ester, acyl, amide, —CO—O—$R_{20}$—D, and —CO—NH—$R_{20}$—D groups in which $R_{20}$ is an alkylene and D is a quaternary ammonium group;

$A_1$ and $B_1$ are chosen from polymethylenic groups containing from 2 to 20 carbon atoms which can be linear or branched, saturated or unsaturated and which can contain, linked to or intercalated in the main chain, at least one aromatic ring, at least one moiety chosen from oxygen, sulphur, sulphoxide, sulphone, disulphide, amino, alkylamino, hydroxyl, quaternary ammonium, ureido, amide, and esters, and $X^-$ is chosen from anions derived from inorganic and organic acids;

$A_1$, $R_{16}$ and $R_{18}$ can form, with the two nitrogen atoms to which they are attached, a piperazine ring; in addition, if $A_1$ is chosen from linear, branched, saturated, and unsaturated alkylene and hydroxyalkylene radicals, $B_1$ can also be chosen from $(CH_2)_n$—CO—D—OC—$(CH_2)_n$— wherein:
n denotes an integer ranging from 1 to 6;
D is chosen from:
a) a glycol residue of formula: —O—Z—O—, in which Z is chosen from linear and branched hydrocarbon-based radicals, and a group corresponding to one of the following formulae:
$(CH_2$—$CH_2$—$O)_x$—$CH_2$—$CH_2$ and
$[CH_2$—$CH(CH_3)$—$O]_{CH2}$—$CH(CH_3)$—
wherein x and y denote an integer from 1 to 4, representing a defined and unique degree of polymerization or any number from 1 to 4 representing an average degree of polymerization;
b) bis-secondary diamine residues such as a piperazine derivatives;
c) bis-primary diamine residues of formula: —NH—Y—NH—wherein Y is chosen from linear and branched hydrocarbon-based radicals, and the divalent radical —$CH_2$—$CH_2$—S—S—$CH_2$—$CH_2$—;
d) a ureylene group of formula: —NH—CO—NH—.

Suitably, $X^-$ is an anion such as chloride or bromide.

These polymers have a number-average molecular weight generally ranging from 1000 to 100,000.

Polymers of this type are described in particular in French Patent Nos. 2,320,330; 2,270,846; 2,316,271; 2,336,434; and 2,413,907, and U.S. Pat. Nos. 2,273,780; 2,375,853; 2,388,614; 2,454,547; 3,206,462; 2,261,002; 2,271,378; 3,874,870; 4,001,432; 3,929,990; 3,966,904; 4,005,193; 4,025,617; 4,025,627; 4,025,653; 4,026,945; and 4,027,020, the disclosures of which are incorporated by reference herein.

(11) Polyquaternary ammonium polymers comprising units of formula (XI):

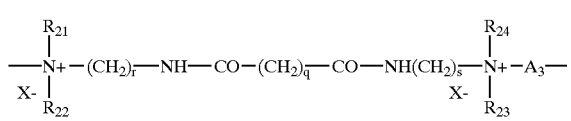

(XI)

wherein:
$R_{21}$, $R_{22}$, $R_{23}$ and $R_{24}$, which may be identical or different, are independently chosen from hydrogen, methyl, ethyl, propyl, β-hydroxyethyl, β-hydroxypropyl, and —$CH_2CH_2(OCH_2CH_2)_p$OH radicals, wherein:
p is an integer ranging from 0 to 6, with the proviso that $R_{21}$, $R_{22}$, $R_{23}$ and $R_{24}$ do not simultaneously represent a hydrogen atom,
r and s, which may be identical or different, are integers ranging from 1 to 6,
q is an integer ranging from 0 to 34,
X denotes a halogen,
$A_3$ is chosen from dihalide radicals and —$CH_2$—$CH_2$—O—$CH_2$—$CH_2$—.

Such compounds are described in particular in European Patent Application No. EP-A-122 324, the disclosure of which is incorporated by reference herein.

Among the products which may be mentioned, for example, are "MIRAPOL A 15", "MIRAPOL AD1", "MIRAPOL AZ1," and "MIRAPOL 175" sold by Miranol.

(12) Homopolymers or copolymers derived from at least one monomer chosen from acrylic and methacrylic acids and comprising units of formulae (XII), (XIII), and (XIV):

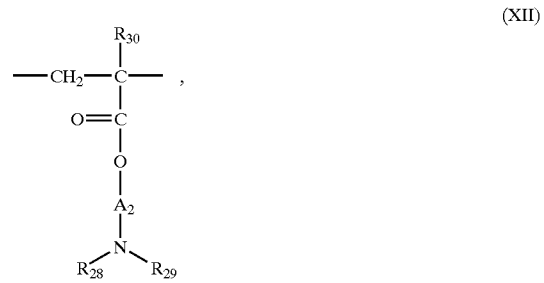

(XII)

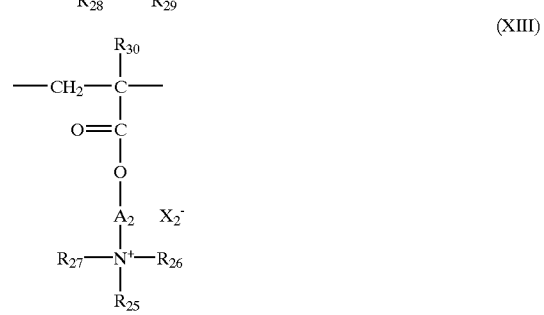

(XIII)

and/or

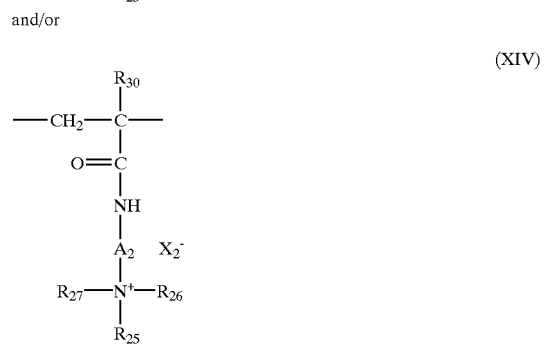

(XIV)

wherein:
$R_{30}$ is independently chosen from H and $CH_3$,
the groups $A_2$ are independently chosen from linear and branched alkyl groups having 1 to 6 carbon atoms, and hydroxyalkyl groups having 1 to 4 carbon atoms,
the groups $R_{25}$, $R_{26}$ and $R_{27}$, which may be identical or different, are independently chosen from alkyl groups having 1 to 18 carbon atoms, and a benzyl radical,
the groups $R_{28}$, and $R_{29}$, are chosen from hydrogen and alkyl groups having 1 to 6 carbon atoms, $X_2^-$ denotes an anion, for example methosulphate or halide, such as chloride or bromide.

The comonomer(s) which can be used to prepare the corresponding copolymers belong to the family of acrylamides, methacrylamides, diacetoneacrylamides, acrylamides, and methacrylamides substituted on the nitrogen with lower alkyls, alkyl esters, acrylic or methacrylic acids, vinylpyrrolidone or vinyl esters.

(13) Quaternary vinylpyrrolidone and vinylimidazole polymers such as, for example, the products sold under the names LUVIQUAT FC 905, LUVIQUAT FC 550, and LUVIQUAT FC 370 by BASF.

(14) Polyamines such as POLYQUART H sold by Henkel, referred to under the name "Polyethylene glycol (15) tallow polyamine" in the CTFA dictionary.

(15) Crosslinked methacryloyloxyethyltrimethylammonium chloride polymers such as the polymers obtained by homopolymerization of dimethylaminoethyl methacrylate quaternized with methyl chloride, or by copolymerization of acrylamide with dimethylaminoethyl methacrylate quaternized with methyl chloride, the homo- or copolymerization being followed by crosslinking with a compound containing olefinic unsaturation, in particular methylenebisacrylamide.

An acrylamide/methacryloyloxyethyltrimethylammonium chloride crosslinked copolymer (20/80 by weight) in the form of a dispersion containing 50% by weight of the said copolymer in mineral oil can be used. This dispersion is sold under the name "SALCARE SC 92" by Allied Colloids. A methacryloyloxyethyltrimethylammonium chloride crosslinked homopolymer containing about 50% by weight of the homopolymer in mineral oil can also be used. This dispersion is sold under the name "SALCARE SC 95" by Allied Colloids.

Other cationic polymers which can be used in the context of the invention include polyalkyleneimines such as polyethyleneimines, polymers containing vinylpyridine or vinylpyridinium units, condensates of polyamines and of epichlorohydrin, polyquaternary ureylenes and chitin derivatives.

Among all the cationic polymers which can be used in the context of the present invention, and according to one embodiment, use may be made of cyclopolymers, such as the copolymers of dimethyidiallylammonium chloride and of acrylamide with a molecular weight greater than 500,000, sold under the names "MERQUAT 550" and "MERQUAT S" by Merck, cationic polysaccharides and, suitably, the polymer sold under the name "JAGUAR C13S" by Meyhall, and the polyaminoamides of the family (6) described above.

According to the invention, cationic polymers in the form of a latex or a pseudolatex, i.e. in the form of a dispersion of insoluble polymer particles, can also be used.

According to the invention, the cationic polymer(s) can be present in an amount ranging from 0.01% to 20% by weight. In another embodiment, the cationic polymer(s) may be present in an amount ranging from 0.01% to 15% by weight; in another embodiment, the amount may range from 0.1% to 5% by weight, relative to the total weight of the composition.

The cationic charge of the cationic polymer(s)/anionic charge of the anionic polymer(s) ratio, expressed in meq./g, generally ranges from 0.25 to 5. In a certain embodiment, the ratio ranges from 0.5 to 2. In yet another embodiment, the ratio ranges from 0.75 to 1.25.

The cationic charge is the number of quaternary, tertiary, secondary, or primary amine atoms per gram of polymer.

The cationic polymer can be a hydroxy($C_1$–$C_4$) alkylcellulose comprising quaternary ammonium groups, such as a hydroxyethylcellulose crosslinked with epichlorohydrin quaternized with trimethylamine; the anionic polymer can be a poly(sodium methacrylate).

The composition according to the invention can also comprise at least one wax. The wax can be chosen from waxes of animal origin, waxes of plant origin, waxes of mineral origin, synthetic waxes, and various fractions of waxes of natural origin. The waxes can be present in an amount ranging from 2% to 40% by weight, relative to the total weight of the composition. In another embodiment, the waxes can be present in an amount ranging from 5% to 30% by weight. In yet another embodiment, the amount can range from 10% to 25% by weight.

The wax can be chosen from waxes (I) having a melting point ranging from 70° C. to 110° C. These waxes in particular have a needle penetration ranging from 1 to 7.5. The needle penetration of waxes is determined according to French standard NF T 60-123 or US ASTM standard D 1321, at a temperature of 25° C. According to these standards, the needle penetration is the measurement of the depth, expressed in tenths of a millimeter, to which a standardized needle weighing 2.5 g, mounted in a mobile assembly weighing 97.5 g and placed on the wax to be tested, for 5 seconds, penetrates into the wax.

The waxes (I) can be chosen, for example, from rice bran wax, carnauba wax, ouricury wax, candelilla wax, montan waxes, sugarcane waxes, and certain polyethylene waxes which satisfy the criteria of the waxes (I).

The composition according to the invention can comprise an amount of waxes (I) ranging from 0.1% to 20% by weight, relative to the total weight of the composition. In an additional embodiment, the amount can range from 1% to 10% by weight.

According to one embodiment of the composition according to the invention, the composition can comprise at least one wax chosen from waxes (Ia) having melting points of greater than or equal to 70° C. and less than 83° C. and waxes (Ib) having a melting point ranging from 83° C. to 110° C.

Waxes (Ia) which may be mentioned include, for example, rice bran wax and candelilla wax. Waxes (Ib) which may be mentioned include, for example, carnauba wax, ouricury wax, and montan waxes. In one embodiment according to the invention, carnauba wax is used.

The composition according to the invention can comprise a mixture of waxes (I) containing at least one first wax (Ia) and at least one second wax (Ib) as defined above.

The said mixture of waxes (I) can comprise from 5% to 50% by weight of wax (Ia), relative to the total weight of the said mixture of waxes (I) and from 50% to 95% by weight of wax (Ib).

The composition can also comprise at least one wax (II), known as a soft wax, having a melting point of greater than or equal to 45° C. and less than 70° C. The wax (II) can have a needle penetration of greater than 7.5, and suitably less than or equal to 217, measured according to the conditions defined previously for waxes (I). This wax (II) makes it possible in particular to soften the coating deposited on the eyelashes.

The waxes (II) can be chosen, for example, from beeswax, lanolin waxes, paraffin waxes, cerasin waxes, microcrystalline waxes, ozokerites, spermacetis, certain polyethylene waxes whose molecular weight is such that they satisfy the criteria of the waxes (II), and hydrogenated plant oils.

Among the hydrogenated plant oils which may be mentioned are hydrogenated jojoba waxes and hydrogenated oils which are obtained by catalytic hydrogenation of fatty substances composed of a linear or non-linear $C_8$–$C_{32}$ fatty chain and which have the qualities corresponding to the definition of the waxes. Mention may be made of hydrogenated sunflower oil, hydrogenated castor oil, hydrogenated cotton oil, hydrogenated copra oil, and hydrogenated lanolin.

The wax (I) and the wax (II) may be present in the composition in a wax (I)/wax (II) weight ratio which can range from 0.2:1 to 1:1. In another embodiment, the ratio can range from 0.4:1 to 0.7:1.

The composition can also contain at least one nonionic film-forming polymer, other than the (meth)acrylate polymer described above, in an amount ranging from 0% to 15% by weight. In another embodiment, the amount ranges from 0.1% to 15% by weight, relative to the total weight of the composition. In yet another embodiment, the amount ranges from 0.1% to 10% by weight.

Nonionic film-forming polymers which may be mentioned, for example, include:
- cellulose polymers such as hydroxyethylcellulose, hydroxypropylcellulose, hydroxypropylethylcellulose and ethylhydroxyethylcellulose;
- acrylic ester polymers or copolymers, such as polyacrylates or polymethacrylates;
- vinyl polymers, such as polyvinylpyrrolidones and copolymers of vinylpyrrolidone and of vinyl acetate; polyvinyl alcohol;
- polyesters, polyamides and epoxy ester resins;
- polyurethane, polyurethane-polyvinylpyrrolidone, polyester-polyurethane, polyether-polyurethane, polyurea, and polyurea/polyurethane polymers,
- polymers of natural origin, which are optionally modified, such as gum arabics, guar gum, xanthan derivatives, and karaya gum;
- and mixtures thereof.

The composition may comprise a polyoxyalkylenated silicone, chosen from silicones comprising a pendant or terminal polyoxyalkylenated chain, or alternatively a polyoxyalkylenated block. Polyoxyalkylenated chains or blocks which may be mentioned include polyoxyethylenated or polyoxypropylenated chains or blocks.

The polyoxyalkylenated silicone can be chosen from the compounds of general formula (XV):

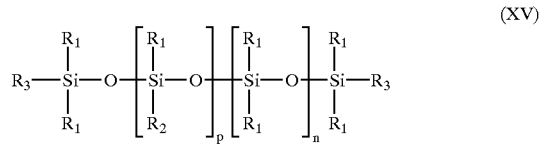

(XV)

wherein:
- $R_1$, which may be identical or different, is independently chosen from hydrogen, linear and branched $C_1$–$C_{30}$ alkyl radicals, and a phenyl radical;
- $R_2$, which may be identical or different, is independently chosen from $R_1$ and A=—$(C_xH_{2x})$—$(OC_2H_4)_a$—$(OC_3H_6)_b$—$OR_4$,
- $R_3$, which may be identical or different, is independently chosen from $R_1$ and A, with $R_2$ being different from $R_3$ when $R_2$=A or $R_3$=A,
- $R_4$, which may be identical or different, is independently chosen from hydrogen, linear and branched alkyl radicals containing from 1 to 12 carbon atoms, and linear and branched acyl radicals containing from 2 to 6 carbon atoms,
- n ranges from 0 to 1000,
- p ranges from 1 to 50,
- a ranges from 0 to 50,
- b ranges from 0 to 50,
- a+b is greater than or equal to 1,
- x ranges from 1 to 5,
- the number-average molecular weight being greater than or equal to 900; in one embodiment, the number-average molecular weight ranges from 2000 to 75,000,
- and mixtures thereof.

Suitably, the polyoxyalkylenated silicone can be a (di)methicone copolyol.

In one embodiment, polyoxyalkylenated silicones of general formula (XV), which correspond to at least one, and possibly all, of the conditions below are used:
- $R_1$ denotes a methyl radical,
- $R_2$=A,
- $R_3$=$R_1$,
- $R_4$ is chosen from hydrogen, a methyl radical, and an acetyl radical; in one embodiment, $R_4$ is hydrogen,
- p ranges from 8 to 20,
- a ranges from 5 to 40; in one embodiment, a ranges from 15 to 30,
- b ranges from 5 to 40; in one embodiment, b ranges from 15 to 30,
- x is equal to 2 or 3,
- n ranges from 20 to 600. In one embodiment, n ranges from 50 to 500; in yet another embodiment, n ranges from 100 to 300,
- and mixtures thereof.

Such silicones are described, for example, in U.S. Pat. No. 4,311,695, the disclosure of which is incorporated by reference herein.

A number of polyoxyalkylenated silicones were presented in particular by Dow Corning during the 17th international congress of the IFSCC in October 1992 and are reported in the article *Water-Soluble Dimethicone Copolyol Waxes for Personal Care Industry* by Linda Madore et al., pages 1 to 3. Those described in European Patent Application No. EP-A-331 833, the disclosure of which is incorporated by reference herein.

These polyoxyalkylenated silicones are polydimethylsiloxanes (PDMSs) comprising one or more water-soluble ether functions (oxyalkylene, such as oxyethylene and/or oxypropylene).

Such polyoxyalkylenated silicones are sold by the company Goldschmidt under the names ABIL B8851, ABIL B88183, ABIL WE09, ABIL EM90 and ABIL EM97. Mention may also be made of the compounds KF 351 to 354 and KF 615 A sold by Shin Etsu, or DMC 6038 sold by Wacker.

The dimethicone copolyol derivatives which can be used include, for example, dimethicone copolyols containing a phosphate, sulphate, myristamide propyldimethylammonium chloride, stearate, amine, and glycomodified groups, to name a few. Dimethicone copolyol derivatives which can be used include those compounds sold by Siltech under the names SILPHOS A100, SILTECH AMINE 65, SILWAX WDIS, and MYRISTAMIDO SILICONE QUAT, or by Phoenix under the name PECOSIL PS 100.

The derivatives sold by Wacker under the name BELSIL DMC6031, or by Dow Corning under the name 2501 cosmetic wax can also be used.

Suitably, polyoxyalkylenated silicone can be nonionic.

The polyoxyalkylenated silicones which may be used include, for example, those sold Dow Corning under the trade name Q2-5220 and by Rhône-Poulenc (now Aventis Pharma S.A.) under the name MIRASIL DMCO.

When the anionic polymer is a silicone, the polyoxyalkylenated silicone according to the invention will be different from the said anionic polymer and, for example, a nonionic silicone. As a specific example, the anionic polymer can be a dimethicone copolyol containing a phosphate group, such as PECOSIL PS100, and the polyoxyethylenated silicone can be a nonionic dimethicone copolyol such as ABIL EM 90 or EM 97.

When the polyoxyalkylenated silicone comprises at least one polyoxyalkylenated block, linear polysiloxane-polyoxyalkylene block copolymers can be used, such as those corresponding to the general formula (XVI):

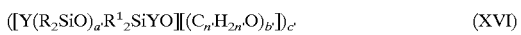  (XVI)

wherein:

R and R', which may be identical or different, are independently chosen from monovalent hydrocarbon-based radicals containing no aliphatic unsaturation, n' is an integer ranging from 2 to 4, a' is an integer greater than or equal to 5, b' is an integer greater than or equal to 4, c' is an integer greater than or equal to 4, Y represents a divalent organic group which is linked to the adjacent silicon atom via a carbon-silicon bond and to a polyoxyalkylene block via an oxygen atom, the average molecular weight of each siloxane block ranges from about 400 to about 10,000, and that of each polyoxyalkylene block ranges from about 300 to about 10,000, the siloxane blocks represent from about 10% to about 90% of the weight of the block copolymer, the average molecular weight of the block copolymer being at least 3000, and mixtures thereof.

The radicals R and R' are suitably chosen from alkyl radicals such as, for example, methyl, ethyl, propyl, butyl, pentyl, hexyl, octyl, decyl, and dodecyl radicals; aryl radicals such as, for example, phenyl and naphthyl radicals; aralkyl radicals such as, for example, benzyl and phenylethyl radicals; tolyl, xylyl and cyclohexyl radicals.

The divalent radical Y is suitably chosen from —R"—, —R"—CO—, —R"—NHCO—, —R"—NH—CO—NH—R"—NHCO, and —R"—OCONH—R"—NHCO—, in which R" is a divalent alkylene group such as, for example, ethylene, propylene, or butylene and R' is a divalent alkylene group or a divalent arylene group such as, for example, —C₆H₄—, —C₆H₄—C₆H₄—, —C₆H₄—CH₂—C₆H₄—or —C₆H₄—CH(CH₃)₂—C₆H₄—.

According to one embodiment, Y represents a divalent alkylene radical, such as a —CH₂—CH₂—CH₂— radical.

The preparation of the block copolymers used according to the present invention is described in particular in European Patent Application No. EP-0 492 657 A1, the disclosure of which is incorporated by reference herein.

According to one specific embodiment of the invention, the block copolymer is chosen from the following copolymers:

[[(CH₃)₂SiO]₄₁(CH₃)₂SiCH₂CH(CH₃)CH₂—O(C₂H₄O)₁₈—(C₃H₆O)₃₃CH₂CH(CH₃)CH₂]₁₆.₁

[[(CH₃)₂SiO]₃₁(CH₃)₂SiCH₂CH(CH₃)CH₂—O(C₂H₄O)₂₀—(C₃H₆O)₂₉CH₂CH(CH₃)CH₂]₁₃.₃

[[(CH₃)₂SiO]₉(CH₃)₂SiCH₂CH(CH₃)CH₂—O(C₂H₄O)₂₀—(C₃H₆O)₂₉CH₂CH(CH₃)CH₂]₂₆.₃

[[(CH₃)₂SiO]₁₆(CH₃)₂SiCH₂CH(CH₃)CH₂—O(C₂H₄O)₁₈—(C₃H₆O)₂₀CH₂CH(CH₃)CH₂]₂₁.₅

[[(CH₃)₂SiO]₉(CH₃)₂SiCH₂CH(CH₃)CH₂—O(C₂H₄O)₅—CH₂CH(CH₃)CH₂]₄.₈

The decimal values correspond to mixtures of compounds of formula (XVI) and of different value c'.

The silicone agents used in the compositions of the invention can be water-soluble or liposoluble.

In the composition according to the invention, the polyoxyalkylenated silicone can be present in an amount ranging from 0.01 to 5% by weight, relative to the total weight of the composition. In one embodiment, the amount can range from 0.1 to 1.5% by weight.

The composition can comprise from 10 to 30% of polyoxyalkylenated silicone by weight relative to the total weight of film-forming polymer.

The composition according to the invention can comprise water and can be in the form of a wax-in-water, water-in-wax, oil-in-water or water-in-oil dispersion. The water content in the composition can range from 1 to 95% by weight, relative to the total weight of the composition, and, according to a certain embodiment, the amount can range from 10 to 80% by weight.

The composition according to the invention can also comprise at least one volatile oil. The expression "volatile oil" means an oil capable of evaporating at room temperature from a support onto which it has been applied, in other words an oil with a measurable vapour pressure at room temperature.

One or more oils that are volatile at room temperature and atmospheric pressure having, for example, a vapour pressure, at ambient pressure and temperature >0 mmHg (0 Pa) and in particular ranging from 10⁻³ to 300 mmHg (0.13 Pa to 40,000 Pa) can be used, provided that the boiling point is greater than 30° C. These volatile oils are favorable for obtaining a film with total "transfer-resistance" properties and good staying power. These volatile oils also make it easier to apply the composition to the skin, mucous membranes, or superficial body growths. These oils can be chosen from hydrocarbon-based oils, silicone oils, fluoro oils, and mixtures thereof.

The expression "hydrocarbon-based oil" means an oil mainly containing hydrogen and carbon atoms and possibly oxygen, nitrogen, sulphur, or phosphorus atoms. Examples of volatile hydrocarbon-based oils which are suitable for the composition according to the invention include hydrocarbon-based oils containing from 8 to 16 carbon atoms, such as C₈–C₁₆ isoalkanes (or isoparaffins) and C₈–C₁₆ branched esters, such as isododecane (also known as 2,2,4,4,6-pentamethylheptane), isodecane, isohexadecane, and isohexyl neopentanoate, and mixtures thereof. Other volatile hydrocarbon-based oils such as petroleum distillates, including those sold under the name SHELL SOLT by Shell, can also be used.

Volatile oils which can also be used are volatile silicones such as, for example, cyclic and volatile silicone oils, including those with a viscosity ≦8 centistokes (8×10⁻⁶ m²/s), such as octamethylcyclotetrasiloxane, decamethylcyclopentasiloxane, docadecamethylcyclohexasiloxane, volatile linear silicones such as octamethyltrisiloxane, heptamethylhexyltrisiloxane, heptamethyloctyltrisiloxane, and decamethyltetrasiloxane or alternatively volatile fluoro oils such as nonafluoromethoxybutane or perfluoromethylcyclopentane.

The volatile oil can be present in the composition according to the invention in an amount ranging from 0% to 80% by weight relative to the total weight of the composition. According to a certain embodiment, the amount may range from 1% to 80%. In another embodiment, the amount may range from 0% to 65% by weight. In yet another embodiment, the amount may range from 1% to 65%.

The composition can also comprise at least one non-volatile oil chosen in particular from non-volatile hydrocarbon-based and/or silicone and/or fluoro oils.

Non-volatile hydrocarbon-based oils which can be mentioned include:

hydrocarbon-based oils of animal origin, such as perhydrosqualene;

hydrocarbon-based oils of plant origin, such as liquid triglycerides of fatty acids containing from 4 to 10 carbon atoms, such as heptanoic or octanoic acid triglycerides, or alternatively sunflower oil, grape seed oil, sesame oil, corn oil, apricot oil, castor oil, avocado oil, olive oil, cereal germ oil, soybean oil, sweet almond oil, palm oil, rape seed oil, cotton oil, hazelnut oil, macadamia oil, jojoba oil, caprylic/capric acid triglycerides such as those sold by Stéarineries Dubois or those sold under the names MIGLYOL 810, MIGLYOL 812, and MIGLYOL 818 by Dynamit Nobel, and karite butter oil;

linear or branched hydrocarbons of mineral or synthetic origin, such as petroleum jelly, polydecenes, and hydrogenated polyisobutene such as parleam;

synthetic esters and ethers such as the oils of formula $R_1COOR_2$ in which $R_1$ is chosen from higher fatty acid residues comprising from 6 to 29 carbon atoms, and $R_2$ is chosen from hydrocarbon-based chains containing from 3 to 30 carbon atoms, such as purcellin oil, isopropyl myristate, isopropyl palmitate, butyl stearate, hexyl laurate, diisopropyl adipate, isononyl isononate, 2-ethylhexyl palmitate, 2-hexyldecyl laurate, 2-octyldecyl palmitate, and 2-octyldodecyl myristate or lactate; polyol esters such as propylene glycol dioctanoate, neopentyl glycol diheptanoate and diethylene glycol diisonanoate and pentaerythritol esters;

fatty alcohols that are liquid at room temperature, containing a branched and/or unsaturated carbon-based chain containing from 12 to 26 carbon atoms, such as octyldodecanol, isostearyl alcohol, oleyl alcohol, 2-hexyldecanol, 2-butyloctanol or 2-undecylpentadecanol;

high fatty acids, such as myristic acid, palmitic acid, stearic acid, behenic acid, oleic acid, linoleic acid, linolenic acid or isostearic acid; and mixtures thereof.

The non-volatile silicone oils which can be used in the composition according to the invention can be oils of low viscosity, such as linear polysiloxanes whose degree of polymerization ranges from approximately 6 to 2000. Mention may be made, for example, of polydimethylsiloxanes (PDMSs) with a viscosity greater than 10 mPa.s, phenyl dimethicones, phenyl trimethicones, polyphenylmethylsiloxanes, and mixtures thereof.

The fluoro oils which can be used in the invention are, for example, fluorosilicone oils, polyfluoro ethers, and fluorosilicones as described in European Patent Application No. EP-A-847 752.

The non-volatile oils can be present in the composition according to the invention in a content ranging from 0% to 50% by weight relative to the total weight of the composition. In another embodiment, the amount may range from 0.1 to 50% by weight. In yet another embodiment, the amount may range from 0% to 20% by weight. In still a further embodiment, the amount may range from 0.1% to 20% by weight.

The composition according to the invention can contain emulsifying surfactants present in a proportion ranging from 2 to 30% by weight relative to the total weight of the composition. In another embodiment, the amount may range from 5% to 15%. These surfactants can be chosen from anionic and nonionic surfactants. Reference may be made to the "*Encyclopedia of Chemical Technology, Kirk-Othmer*", Volume 22, pp. 333–432, 3rd edition, 1979, Wiley, for the definition of the properties and functions (emulsifying) of the surfactants, in particular pp. 347–377 of this reference, for the anionic and nonionic surfactants.

The surfactants which may be used in the composition according to the invention are chosen:

from nonionic surfactants: fatty acids, fatty alcohols, polyethoxylated or polyglycerolated fatty alcohols such as polyethoxylated stearyl or cetylstearyl alcohol, fatty acid esters of sucrose, alkyl glucose esters such as, for example, polyoxyethylenated fatty esters of $C_1$–$C_6$ alkyl glucose, and mixtures thereof;

from anionic surfactants: $C_{16}$–$C_{30}$ fatty acids neutralized with amines, aqueous ammonia, alkaline salts, and mixtures thereof.

Surfactants which make it possible to obtain an oil-in-water or wax-in-water emulsion may be used.

The composition can also comprise at least one dyestuff such as pulverulent compounds, for example in a proportion of from 0.01 to 25% of the total weight of the composition. The pulverulent compounds can be chosen from the pigments and/or nacres and/or fillers usually used in mascaras.

The pigments can be white or coloured, and inorganic and/or organic. Among the inorganic pigments which may be mentioned are titanium dioxide, which has optionally been surface-treated, zirconium oxide or cerium oxide, as well as iron oxide or chromium oxide, manganese violet, ultramarine blue, chromium hydrate and ferric blue. Among the organic pigments which may be mentioned are carbon black, pigments of D & C type, and lakes based on cochineal carmine, barium, strontium, calcium or aluminium.

The nacreous pigments can be chosen from white nacreous pigments such as mica coated with titanium or with bismuth oxychloride, coloured nacreous pigments such as titanium mica with iron oxides, titanium mica with, for example, ferric blue or chromium oxide, titanium mica with an organic pigment of the abovementioned type, and nacreous pigments based on bismuth oxychloride.

The fillers can be chosen from those which are well-known to those skilled in the art and which are commonly used in cosmetic compositions. Fillers which may be used include:

talc, which is a hydrated magnesium silicate used in the form of particles generally less than 40 microns, micas, which are aluminosilicates of varied composition, in the form of flakes from 2 to 200 microns in size. In one embodiment, the flakes range from 5 to 70 microns in size, and between 0.1 and 5 microns thick, suitably from 0.2 to 3 microns thick, it being possible for these micas to be of natural origin, such as muscovite, margarite, roscoelite, lipidolite or biotite, or of synthetic orgin, starch, in particular rice starch, kaolin, which is a hydrated aluminium silicate, present in the form of particles of isotropic form which are generally less than 30 microns in size, zinc oxide and titanium oxide, which are generally used in the form of particles not exceeding a few microns in size, calcium carbonate, magnesium carbonate or magnesium hydrocarbonate, microcrystalline cellulose, silica, synthetic polymer powders such as polyethylene, polyesters (polyethylene isophthalate or terephthalate), polyamides such as those sold under the trade name "NYLON" or "TEFLON", and silicone powders.

The composition according to the invention can also contain ingredients commonly used in cosmetics, such as trace elements, softeners, sequestering agents, fragrances, oils, silicones, thickeners, vitamins, proteins, ceramides, plasticizers and cohesion agents, as well as the basifying or acidifying agents usually used in cosmetics, emollients and preserving agents.

Needless to say, a person skilled in the art will take care to select this or these optional additional compound(s), and/or the amount thereof, such that the advantageous properties of the composition according to the invention are not, or are not substantially, adversely affected by the addition envisaged.

The composition according to the invention can be prepared according to the usual methods of the fields under consideration.

EXAMPLE

The invention is illustrated in greater detail in the following example:

A mascara having the following composition was prepared:

| | |
|---|---|
| Carnauba wax | 7 g |
| Beeswax | 8 g |
| Rice bran wax | 7 g |
| Candelilla wax | 2.5 g |
| 2-Amino-2-methyl-1,3-propanediol | 0.2 g |
| Triethanolamine | 2.4 g |
| Stearic acid | 5.4 g |
| Water-soluble nonionic polymers | 1.72 g |
| Ethyl acrylate/methyl methacrylate copolymer (80/20) as an aqueous dispersion containing 50% AM (DAITOSOL 5000 AD from Saito) | 0.75 g AM |
| Dimethicone copolyol (Q2-5220 from Dow Corning) | 0.2 g |
| Poly(sodium methacrylate) (DARVAN 7 from Vanderbilt) | 0.25 g AM |
| Hydroxyethylcellulose crosslinked with epichlorohydrin quaternized with trimethylamine (JR 400 from Union Carbide) | 0.1 g |
| Pigments | 6 g |
| Preserving agents | qs |
| Water | qs 100 g |

The make-up criteria of the composition were evaluated by a panel of 19 women.

Most of the panel considered that the composition adhered to the eyelashes well and was easy to apply. The composition made it possible to obtain a fast make-up result: the eyelashes were lengthened and curled well. The make-up result obtained was comfortable and had good staying power over time (less break down than a prior art mascara); the eyelashes were well separated; the mascara was easy to remove.

The present invention may be embodied in other specific forms without departing from its spirit or essential characteristics. The described embodiments are to be considered in all respects as illustrative only and not restrictive. The scope of the invention is, therefore, indicated by the appended claims, rather than by the foregoing description. All changes which come within the meaning and range of equivalency of the claims are to be embraced within their scope.

What is claimed is:

1. A composition comprising at least one film-forming polymer comprising:

(A) at least one cationic polymer;

(B) at least one anionic polymer; and (C) an aqueous dispersion of at least one $C_1$–$C_6$ alkyl (meth)acrylate nonionic film-forming polymer.

2. A composition according to claim 1, wherein the at least one anionic polymer is noncrosslinked.

3. A composition according to claim 1, wherein the at least one $C_1$–$C_6$ alkyl (meth)acrylate nonionic film-forming polymer is chosen from $C_1$–$C_4$ alkyl (meth)acrylate nonionic film-forming polymers.

4. A composition according to claim 1, wherein the at least one $C_1$–$C_6$ alkyl (meth)acrylate nonionic film-forming polymer is chosen from copolymers derived from at least one monomer chosen from $C_1$–$C_4$ alkyl acrylate and $C_1$–$C_4$ alkyl methacrylate.

5. A composition according to claim 1, wherein the at least one $C_1$–C6 alkyl (meth)acrylate nonionic film-forming polymer is a copolymer derived from at least one monomer chosen from ethyl acrylate and methyl methacrylate.

6. A composition according to claim 1, wherein the at least one $C_1$–$C_6$ alkyl (meth)acrylate nonionic film-forming polymer is present in a solids content ranging from 0.1% to 15% by weight, relative to the total weight of the composition.

7. A composition according to claim 6, wherein the alkyl (meth)acrylate polymer is present in a solids content ranging from 0.5% to 8% by weight.

8. A composition according to claim 1, wherein the at least one anionic polymer is chosen from:

polymers comprising carboxylic units derived from unsaturated mono- or dicarboxylic acid monomers of formula (I):

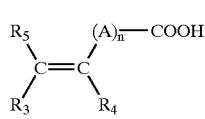

wherein:

n is an integer ranging from 0 to 10;

A is chosen from a methylene group;

$R_5$ is chosen from a hydrogen atom, a phenyl group, and a benzyl group;

$R_3$ is chosen from a hydrogen atom, lower alkyl groups, and carboxyl groups; and $R_4$ is chosen from a hydrogen atom, lower alkyl groups, $CH_2$—COOH, a phenyl group, and a benzyl group; and polymers comprising units derived from sulphonic acid.

9. A composition according to claim 8, wherein A is a methylene group connected to the carbon atom of the unsaturated group or to the neighboring methylene group when n is greater than 1 via a hetero atom chosen from oxygen and sulphur.

10. A composition according to claim 8, wherein the units derived from sulphonic acid are chosen from vinylsulphonic units, styrenesulphonic units, acrylamidoalkylsulphonic units, and sulphonic polyesters.

11. A composition according to claim 1, wherein the at least one anionic polymer is chosen from:
   A) homopolymers and copolymers derived from at least one monomer chosen from acrylic and methacrylic acid and salts of said homopolymers and copolymers, copolymers derived from acrylic acid and acrylamide and salts of said copolymers, and sodium salts of polyhydroxycarboxylic acids;
   B) copolymers derived from (i) at least one monomer chosen from acrylic and methacrylic acids and (ii) a monoethylenic monomer; copolymers derived from at least one monomer chosen from acrylic and methacrylic acids having a chain comprising an acrylamide unit unsubstituted or substituted with at least one group chosen from N-alkylated groups and hydroxyalkylated groups; copolymers derived from at least one monomer chosen from acrylic acid and $C_1$–$C_4$ alkyl methacrylates; and terpolymers derived from vinylpyrrolidone, acrylic acid, and $C_1$–$C_{20}$ alkyl methacrylate;
   C) copolymers derived from crotonic acid;
   D) polymers derived from (i) at least one monomer chosen from maleic, fumaric, and itaconic acids and anhydrides of each of said acids, and (ii) at least one monomer chosen from vinyl esters, vinyl ethers, vinyl halides, phenylvinyl derivatives, and acrylic acid and esters thereof; copolymers derived from (i) at least one monomer chosen from maleic, citraconic, and itaconic anhydrides and (ii) at least one monomer chosen from allylic and methallylic esters;
   E) polyacrylamides comprising carboxylate groups,
   F) deoxyribonucleic acid; and
   G) copolymers derived from at least one dicarboxylic acid, at least one diol, and at least one difunctional aromatic monomer having a group —$SO_3M$ wherein M is chosen from a hydrogen atom, an ammonium ion, and a metal ion.

12. A composition according to claim 11, wherein the monoethylenic monomer is chosen from ethylene, styrene, vinyl esters, acrylic acid esters, and methacrylic acid esters.

13. A composition according to claim 11, wherein the monoethylenic monomer is grafted onto a polyalkylene glycol.

14. A composition according to claim 13, wherein the polyalkylene glycol is polyethylene glycol.

15. A composition according to claim 11, wherein the copolymers derived from crotonic acid comprise at least one unit chosen from vinyl acetate units and propionate units.

16. A composition according to claim 15, wherein the copolymers derived from crotonic acid further comprise at least one monomeric unit chosen from allylic and methallylic esters, vinyl ethers and vinyl esters of saturated, linear, and branched carboxylic acids.

17. A composition according to claim 16, wherein the carboxylic acids comprise at least 5 carbon atoms.

18. A composition according to claim 11, wherein the copolymers are derived from (i) at least one monomer chosen from maleic, citraconic, and itaconic anhydride units and (ii) at least one monomer chosen from allylic and methallylic esters and further comprising in their chain at least one unit derived from at least one monomer chosen from acrylamide, methacrylamide, α-olefin, acrylic and methacrylic esters, acrylic and methacrylic acids, and vinylpyrrolidone, and the anhydride functions are monoesterified or monoamidated.

19. A composition according to claim 11, wherein the copolymers derived from crotonic acid are grafted copolymers.

20. A composition according to claim 1, wherein the at least one anionic polymer is chosen from:
   acrylic and methacrylic acid homopolymers;
   acrylic acid copolymers;
   copolymers derived from crotonic acid;
   polymers derived from (i) at least one monomer chosen from maleic, fumaric, and itaconic acid and anhydrides of said acids and (ii) at least one monomer chosen from vinyl esters, vinyl ethers, vinyl halides, phenylvinyl derivatives, acrylic acid, and acrylic acid esters;
   copolymers derived from at least one monomer chosen from methacrylic acid and methyl methacrylate;
   copolymers derived from at least one monomer chosen from methacrylic acid and ethyl acrylate;
   terpolymers of vinylpyrrolidone/acrylic acid/lauryl methacrylate;
   vinyl acetate/crotonic acid copolymers;
   vinyl acetate/crotonic acid/polyethylene glycol terpolymers; and
   sulphopolyesters obtained by condensation of diethylene glycol, cyclohexanedimethanol, isophthalic acid, and sulphoisophthalic acid.

21. A composition according to claim 1, wherein the at least one anionic polymer is chosen from acrylic acid/ethyl acrylate/N-tert-butylacrylamide terpolymer.

22. A composition according to claim 20, wherein the copolymers derived from crotonic acid are chosen from vinyl acetate/vinyl tert-butylbenzoate/crotonic acid terpolymers and crotonic acid/vinyl acetate/vinyl neododecanoate terpolymers.

23. A composition according to claim 1, wherein the at least one anionic polymer is chosen from methyl vinyl ether/monoesterified maleic anhydride copolymers.

24. A composition according to claim 1, wherein the at least one anionic polymer is chosen from grafted silicone anionic polymers comprising:
   a polysiloxane portion, and
   a non-silicone organic chain portion, with one of the two portions constituting the main chain of the polymer, the other being grafted onto the said main chain.

25. A composition according to claim 24, wherein the grafted silicone anionic polymers are chosen from silicone polymers whose structure comprises the unit of formula (III):

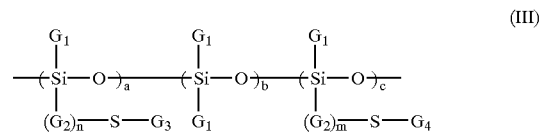

(III)

wherein:
   the radicals $G_1$, which are identical or different, are independently chosen from hydrogen, $C_1$–$C_{10}$ alkyl radicals, and a phenyl radical;
   the radicals $G_2$, which are identical or different, are independently chosen from a $C_1$–$C_{10}$ alkylene group;
   $G_3$ is chosen from polymeric residues resulting from the (homo)polymerization of at least one anionic monomer containing ethylenic unsaturation, said residues being identical or different if $a \geq 2$;
   $G_4$ is chosen from polymeric residues resulting from the (homo)polymerization of at least one hydrophobic monomer containing ethylenic unsaturation, said residues being identical or different if $a \geq 2$;

m and n are equal to 0 or 1;

a is an integer ranging from 0 to 50;

b is an integer ranging from 10 to 350; and c is an integer ranging from 0 to 50; with the proviso that one of the parameters a and c is other than 0.

26. A composition according to claim 25, wherein the unit of formula (III) has at least one of the following characteristics:

the radicals $G_1$ are chosen from $C_1$–$C_{10}$ alkyl radicals;

n is non-zero and the radicals $G_2$ are chosen from divalent $C_1$–$C_3$ radicals;

$G_3$ is chosen from polymeric radicals resulting from the (homo)polymerization of at least one monomer chosen from carboxylic acids containing ethylenic unsaturation;

$G_4$ is chosen from polymeric residues resulting from the (homo)polymerization of at least one monomer chosen from $C_1$–$C_{10}$ alkyl (meth)acrylates.

27. A composition according to claim 25, wherein, for the unit of formula (III):

$G_1$ is a methyl radical;

n is non-zero and $G_2$ is a propylene radical;

$G_3$ is chosen from polymeric radicals resulting from the (homo)polymerization of a monomer chosen from acrylic acid and methacrylic acid;

$G_4$ is chosen from polymeric radicals resulting from the (homo)polymerization of a monomer chosen from isobutyl and methyl (meth)acrylate.

28. A composition according to claim 1, wherein the at least one anionic polymer is in a form chosen from a latex and a pseudolatex.

29. A composition according to claim 1, wherein the at least one cationic polymer is chosen from quaternary cellulose ether derivatives, copolymers derived from (i) at least one cellulose and (ii) a water-soluble quaternary ammonium monomer, cyclopolymers, cationic polysaccharides, cationic silicone polymers, quaternized and non-quaternized vinylpyrrolidone-dialkylaminoalkyl acrylate and methacrylate copolymers, quaternary polymers derived from vinylpyrrolidone and vinylimidazole, and polyaminoamides.

30. A composition according to claim 1, wherein the at least one anionic polymer is a poly(sodium methacrylate).

31. A composition according to claim 1, wherein the at least one cationic polymer is a hydroxy($C_1$–$C_4$)alkyl cellulose comprising quaternary ammonium groups.

32. A composition according to claim 1, wherein the at least one cationic polymer is present in an amount ranging from 0.01% to 20% by weight, relative to the total weight of the composition.

33. A composition according to claim 32, wherein the at least one cationic polymer is present in an amount ranging from 0.01% to 15% by weight.

34. A composition according to claim 33, wherein the at least one cationic polymer is present in an amount ranging from 0.1% to 5% by weight.

35. A composition according to claim 1, wherein the at least one anionic polymer is present in an amount ranging from 0.01 to 20% by weight relative to the total weight of the composition.

36. A composition according to claim 35, wherein the at least one anionic polymer is present in an amount ranging from 0.05 to 15% by weight.

37. A composition according to claim 36, wherein the at least one anionic polymer is present in an amount ranging from 0.1% to 7% by weight.

38. A composition according to claim 1, further comprising at least one wax.

39. A composition according to claim 38, wherein the at least one wax is present in an amount ranging from 2% to 40% by weight, relative to the total weight of the composition.

40. A composition according to claim 39, wherein the at least one wax is present in an amount ranging from 5% to 30% by weight.

41. A composition according to claim 40, wherein the at least one wax is present in an amount ranging from 10% to 25% by weight.

42. A composition according to claim 38, wherein the at least one wax comprises at least one wax (I) having a melting point ranging from 70° C. to 110° C.

43. A composition according to claim 42, wherein the at least one wax (I) is present in an amount ranging from 0.1% to 20% by weight, relative to the total weight of the composition.

44. A composition according to claim 42, further comprising at least one wax (II) having a melting point greater than or equal to 45° C. and less than 70° C.

45. A composition according to claim 44, wherein the at least one wax (II) is present in a wax (I)/wax (II) weight ratio ranging from 0.2:1 to 1:1.

46. A composition according to claim 42, wherein the at least one wax (I) is chosen from rice bran wax, carnauba wax, ouricury wax, candelilla wax, montan waxes, sugarcane waxes, and polyethylene waxes.

47. A composition according to claim 44, wherein the at least one wax (II) is chosen from beeswax, lanolin wax, paraffin waxes, cerasin waxes, microcrystalline waxes, ozokerites, spermacetis, polyethylene waxes, and hydrogenated plant oils.

48. A composition according to claim 1, further comprising at least one polyoxyalkylenated silicone.

49. A composition according to claim 1, further comprising at least one dimethicone copolyol.

50. A composition according to claim 1, further comprising at least one additional nonionic film-forming polymer other than the at least one $C_1$–$C_6$ alkyl (meth)acrylate polymer.

51. A composition according to claim 1, further comprising water in an amount ranging from 1% to 95% by weight, relative to the total weight of the composition.

52. A composition according to claim 51, wherein water is present in an amount ranging from 10 to 80% by weight.

53. A composition according to claim 1 in the form of an emulsion.

54. A composition according to claim 53, wherein the emulsion is in a form chosen from wax-in-water emulsions, water-in-wax emulsions, oil-in-water emulsions, and water-in-oil emulsions.

55. A composition according to claim 1, further comprising at least one volatile oil.

56. A composition according to claim 55, wherein the at least one volatile oil is a volatile silicone oil.

57. A composition according to claim 56, wherein the volatile silicone oil is chosen from octamethylcyclotetrasiloxane, decamethylcyclopentasiloxane, docadecamethylcyclohexasiloxane, octamethyltrisiloxane, heptamethylhexyltrisiloxane, heptamethyloctyltrisiloxane, and decamethyltetrasiloxane.

58. A composition according to claim 1, further comprising at least one emulsifying surfactant.

59. A composition according to claim 58, wherein the at least one emulsifying surfactant is present in an amount ranging from 2% to 30% by weight, relative to the total weight of the composition.

60. A composition according to claim 1, further comprising at least one additive chosen from vitamins, trace elements, softeners, sequestering agents, fragrances, oils, thickeners, proteins, ceramides, plasticizers, cohesion agents, basifying and acidifying agents, fillers, pigments, emollients, and preserving agents.

61. A make-up composition, a make-up base, a composition to be applied over a make-up, or a composition for cosmetically treating keratin fibers comprising:
    (A) at least one cationic polymer;
    (B) at least one anionic polymer; and
    (C) an aqueous dispersion of at least one $C_1$–$C_6$ alkyl (meth)acrylate nonionic film-forming polymer; and at least one additive chosen from vitamins, trace elements, softeners, sequestering agents, fragrances, oils, thickeners, proteins, ceramides, plasticizers, cohesion agents, basifying and acidifying agents, fillers, pigments, emollients, and preserving agents.

62. A process for coating keratin fibers comprising applying to the keratin fibers a composition comprising:
    (A) at least one cationic polymer;
    (B) at least one anionic polymer; and
    (C) an aqueous dispersion of at least one $C_1$–$C_6$ alkyl (meth)acrylate nonionic film-forming polymer.

63. A process for coating eyelashes comprising applying to the eyelashes a composition comprising:
    (A) at least one cationic polymer;
    (B) at least one anionic polymer; and
    (C) an aqueous dispersion of at least one $C_1$–$C_6$ alkyl (meth)acrylate nonionic film-forming polymer.

64. A process for curling eyelashes comprising applying to the eyelashes a composition comprising:
    (A) at least one cationic polymer;
    (B) at least one anionic polymer; and
    (C) an aqueous dispersion of at least one $C_1$–$C_6$ alkyl (meth)acrylate nonionic film-forming polymer.

65. A process for lengthening eyelashes comprising applying to the eyelashes a composition comprising:
    (A) at least one cationic polymer;
    (B) at least one anionic polymer; and
    (C) an aqueous dispersion of at least one $C_1$–$C_6$ alkyl (meth)acrylate nonionic film-forming polymer.

* * * * *